United States Patent [19]
Dyke et al.

[11] Patent Number: 5,972,936
[45] Date of Patent: Oct. 26, 1999

[54] BENZOFURAN CARBOXAMIDES AND THEIR THERAPEUTIC USE

[75] Inventors: Hazel Joan Dyke; John Gary Montana, both of Cambridge, United Kingdom

[73] Assignee: Darwin Discover Limited, United Kingdom

[21] Appl. No.: 08/859,510

[22] Filed: May 20, 1997

[30] Foreign Application Priority Data

May 20, 1996 [GB] United Kingdom .................... 9610515
Dec. 5, 1996 [WO] WIPO ...................... PCT/GB96/03012
Apr. 22, 1997 [GB] United Kingdom .................... 9708070

[51] Int. Cl.$^6$ ...................... C07D 307/83; C07D 401/12; A61K 31/34
[52] U.S. Cl. ...................... 514/233.5; 514/333; 514/337; 514/342; 514/469; 514/470; 544/124; 546/256; 546/269.7; 546/271.1; 546/284.1; 549/462; 549/466; 549/467; 549/468
[58] Field of Search ...................... 549/462, 466, 549/467, 468; 514/469, 470, 233.5, 333, 337, 342; 544/124; 546/256, 269.7, 271.1, 284.1

[56] References Cited

FOREIGN PATENT DOCUMENTS

| 0637586 | 8/1994 | European Pat. Off. . |
| 0685475 | 5/1995 | European Pat. Off. . |
| 0771794 | 5/1997 | European Pat. Off. . |
| 9203427 | 3/1992 | WIPO . |
| 9408962 | 4/1994 | WIPO . |
| 9636595 | 11/1996 | WIPO . |
| 9636596 | 11/1996 | WIPO . |
| 9636611 | 11/1996 | WIPO . |

OTHER PUBLICATIONS

Damasio, Alzheimer's Disease And Related Dementias, Cecil Textbook of Medicine, 20th Edition, vol. 2, pp. 1992–1996, 1996.
Christensen et al., Chem. Abstract 76:99520, 1972.

*Primary Examiner*—Mukund J. Shah
*Assistant Examiner*—Deepak R. Rao
*Attorney, Agent, or Firm*—Saliwanchik, Lloyd & Saliwanchik

[57] ABSTRACT

Compounds having the formula (i),

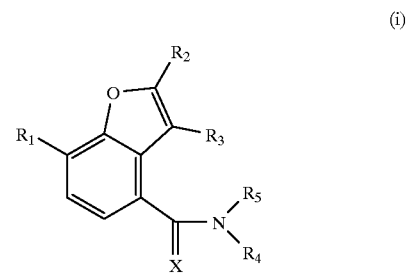

wherein the groups $R_1$, $R_2$, $R_3$, $R_4$ and $R_5$ are defined herein. The compounds of the present invention can be utilized to treat disease states capable of being modulated by inhibition of proteins which mediate cellular activity, such as tumor necrosis factor (TNF) and/or phosphodiesterase IV (PDE IV).

28 Claims, No Drawings

BENZOFURAN CARBOXAMIDES AND THEIR THERAPEUTIC USE

FIELD OF THE INVENTION

The present invention relates to novel benzofuran carboxamides, and to their formulation and use as pharmaceuticals.

BACKGROUND OF THE INVENTION

EP-A-0637586 discloses benzofuran derivatives, including 4-carboxamides, as acetylcholine esterase inhibitors.

WO-A-9408962 discloses benzofuran analogues as fibrinogen receptor antagonists.

WO-A-9203427 discloses benzofuran-2-carboxamides, with a 3-substituent selected from hydroxy, acyloxy, alkoxy, optionally alkyl-substituted aminoalkoxy, alkylsulphonylamino, optionally alkyl-substituted aminoalkylsulphonyl or arylsulphonylamino, as a remedy for osteoporosis.

EP-A-0685475 discloses benzofuran-2-carboxamides as anti-inflammatory agents.

WO-A-9603399 discloses dihydrobenzofuran-4-carboxamides as inhibitors of phosphodiesterases.

Phosphodiesterases (PDE) and Tumour Necrosis Factor (TNF), their modes of action and the therapeutic utilities of inhibitors thereof, are described in WO-A-9636595, WO-A-9636596 and WO-A-9636611, the contents of which are incorporated herein by reference. The same documents disclose benzofuran derivatives having utility as PDE and TNF inhibitors.

SUMMARY OF THE INVENTION

This invention is based on the discovery of novel compounds that can be used to treat disease states, for example disease states associated with proteins that mediate cellular activity, for example disease states associated with proteins that mediate cellular activity, for example by inhibiting tumor necrosis factor and/or by inhibiting phosphodiesterase IV. According to the invention, the novel compounds are of formula (i):

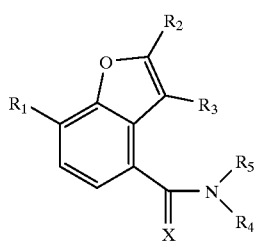

$R_1$ is selected from the group consisting of alkoxy (optionally substituted with one or more halogens), OH and thioalkyl;

$R_2$ and $R_3$, which may be the same or different, are each selected from the group consisting of H, halogen, $OR_{10}$, $CF_3$, $C(=NOR_6)R_6$, alkyl-$C(=NOR_6)R_6$, $COR_{15}$, $NR_8R_9$, heterocyclo optionally substituted with $R_{14}$, heterocycloalkyl optionally substituted with $R_{14}$, heteroarylalkyl optionally substituted with $R_{14}$, alkyl substituted with $R_{16}$ and cycloalkyl substituted with $R_{14}$, with the proviso that $R_2$ is not H;

$R_4$ is selected from the group consisting of H, arylalkyl, heteroarylalkyl, heterocycloalkyl, $S(O)_mR_{10}$ and alkyl optionally substituted with one or more substituents chosen from hydroxy, alkoxy, $CO_2R_7$, $SO_2NR_{11}R_{12}$, $CONR_{11}R_{12}$, —CN, carbonyl oxygen (where appropriate), $NR_8R_9$, $COR_{10}$ and $S(O)_mR_{10}$;

$R_5$ is selected from the group consisting of aryl, heteroaryl, heterocyclo, arylalkyl, heteroarylalkyl and heterocycloalkyl;

in $R_4$ and/or $R_5$, the aryl/heteroaryl/heterocyclo portion may be optionally substituted with one or more substituents alkyl-$R_{13}$ or $R_{13}$;

$R_6$ is selected from the group consisting of H and $R_{10}$ optionally substituted at any position(s) with one or more $R_{14}$;

$R_7$ is selected from the group consisting of H, alkyl, arylalkyl and heteroarylalkyl, heterocycloalkyl;

$R_8$ is selected from the group consisting of H, aryl, heteroaryl, heterocyclo, alkyl, arylalkyl, heteroarylalkyl, heterocycloalkyl, alkylcarbonyl, alkoxycarbonyl, arylsulphonyl, heteroarylsulphonyl, heterocyclosulphonyl, arylcarbonyl, heteroarylcarbonyl, heterocyclocarbonyl and alkylsulphonyl;

$R_{10}$ is selected from the group consisting of alkyl, cycloalkyl, aryl, heteroaryl, heterocyclo, arylalkyl, heteroarylalkyl and heterocycloalkyl;

$R_9$, $R_{11}$ and $R_{12}$, which may be the same or different, are each selected from the group consisting of H and $R_{10}$;

$R_{13}$ is selected from the group consisting of alkyl or alkoxy optionally substituted by halogen, aryl, heteroaryl, heterocyclo, hydroxy, aryloxy, heteroaryloxy, heterocyclooxy, arylalkyloxy, heteroarylalkyloxy, heterocycloalkyloxy, $CO_2R_7$, $CONR_{11}R_{12}$, $SO_2NR_{11}R_{12}$, halogen, —CN, —$NR_8R_9$, $COR_{10}$, $S(O)_nR_{10}$, and carbonyl oxygen (where appropriate;

$R_{14}$ is selected from the group consisting of alkyl, hydroxy, $OR_{10}$, carbonyl oxygen, $NR_8R_9$, CN, $CO_2H$, $CO_2R_{10}$, $CONR_{11}R_{12}$ and $COR_{10}$;

$R_{15}$ is selected from the group consisting of heteroarylalkyl optionally substituted with $R_{14}$, heterocycloalkyl optionally substituted with $R_{14}$, aryl optionally substituted with $R_{14}$, heterocyclo (not attached through nitrogen) optionally substituted with $R_{14}$, and alkyl substituted with $R_{14}$ or cycloalkyl substituted with $R_{14}$;

$R_{16}$ is selected from the group consisting of OH, $OR_{10}$, $NR_8R_9$, CN and $COR_{15}$;

m represents 1 or 2;

n represents 0–2;

X represents O or S;

or a pharmaceutically-acceptable salt thereof.

Combinations of substituents and/or variables are only permissible if such combinations result in stable compounds.

DESCRIPTION OF THE INVENTION

Suitable pharmaceutically-acceptable salts are pharmaceutically-acceptable base salts and pharmaceutically-acceptable acid addition salts. Certain of the compounds of formula (i) which contain an acidic group form base salts. Suitable pharmaceutically-acceptable base salts include metal salts, such as alkali metal salts for example sodium salts, or organic amine salts such as that provided with ethylenediamine.

Certain of the compounds of formula (i) which contain an amino group form acid addition salts. Suitable acid addition salts include pharmaceutically-acceptable inorganic salts such as the sulphate, nitrate, phosphate, borate, hydrochloride and hydrobromide and pharmaceutically-acceptable organic acid addition salts such as acetate, tartrate, maleate, citrate, succinate, benzoate, ascorbate, methanesulphate, α-ketoglutarate, α-glycerophosphate and glucose-1-phosphate. The pharmaceutically-acceptable salts of the compounds of formula (i) are prepared using conventional procedures.

It will be appreciated by those skilled in the art that some of the compounds of formula (i) may exist in more than one tautomeric form. This invention extends to all tautomeric forms.

It will be appreciated that the compounds according to the invention can contain one or more asymmetrically substituted atoms. The presence of one or more of these asymmetric centers in a compound of formula (i) can give rise to stereoisomers, and in each case the invention is to be understood to extend to all such stereoisomers, including enantiomers, and diastereoisomers and mixtures including racemic mixtures thereof.

When used herein the term alkyl whether used alone or when used as a part of another group includes straight and branched chain alkyl groups containing up to 6 atoms. Alkoxy means an alkyl-O- group in which the alkyl group is as previously described. Aryloxy means an aryl-O- group in which the aryl group is as defined below. Heteroaryloxy means a heteroaryl-O- group and heterocyclooxy means a heterocyclo-O- group in which the heteroaryl and heterocyclo group are as defined below. Alkylamino means an alkyl-N- group in which the alkyl group is as previously defined, arylamino means aryl-N- and heteroarylamino means an heteroaryl-N- group (aryl and heteroaryl defined below). Thioalkyl means an alkyl-Sgroup. Cycloalkyl includes a non-aromatic cyclic or multicyclic ring system of about 3 to 10 carbon atoms. The cyclic alkyl may optionally be partially unsaturated. Aryl indicates carbocyclic radicals containing about 6 to 10 carbon atoms. Arylalkyl means an aryl-alkylgroup wherein the aryl and alkyl are as described herein. Heteroarylalkyl means a heteroaryl-alkyl group and heterocycloalkyl means a heterocyclo-alkyl group. Alkylcarbonyl means an alkyl-CO- group in which the alkyl group is as previously described. Arylcarbonyl means an aryl-CO- group in which the aryl group is as previously described. Heteroarylcarbonyl means a heteroaryl-CO- group and heterocyclocarbonyl means a heterocyclo-CO- group. Arylsulphonyl means an aryl-SO$_2$- group in which the aryl group is as previously described. Heteroarylsulphonyl means a heteroaryl-SO$_2$- group and heterocyclosulphonyl means a heterocyclo-SO$_2$- group. Alkoxycarbonyl means an alkyloxy-CO- group in which the alkoxy group is as previously described. Alkylsulphonyl means an alkyl-$_2$- group in which the alkyl group is as previously described. Carbonyl oxygen means a —CO— group. It will be appreciated that a carbonyl oxygen can not be a substituent on an aryl or heteroaryl ring. Carbocyclic ring means about a 5 to about 10 membered monocyclic or multicyclic ring system which may saturated or partially unsaturated. Heterocyclic ring means about a 5 to about a 10 membered monocyclic or multicyclic ring system (which may be saturated or partially unsaturated) wherein one or more of the atoms in the ring system is an element other than carbon chosen from amongst nitrogen, oxygen or sulphur atoms. Heteroaryl means about a 5 to about a 10 membered aromatic monocyclic or multicyclic hydrocarbon ring system in which one or more of the atoms in the ring system is an element other than carbon, chosen from amongst nitrogen, oxygen or sulphur; if desired, a N atom may be in the form of an N-oxide. Heterocyclo means about a 5 to about a 10 membered saturated or partially saturated monocyclic or multicyclic hydrocarbon ring system in which one or more of the atoms in the ring systems is an element other than carbon, chosen from amongst nitrogen, oxygen or sulphur. Halogen means fluorine, chlorine, bromine or iodine.

Compounds of the invention are useful for the treatment of TNF mediated disease states. "TNF mediated disease or disease states" means any and all disease states in which TNF plays a role, either by production of TNF itself, or by TNF causing another cytokine to be released, such as but not limited to IL-1 or IL-6. A disease state in which IL-1, for instance, is a major component, and whose production or action is exacerbated or secreted in response to TNF, would therefore be considered a disease state mediated by TNF. As TNF-β (also known as lymphotoxin) has close structure homology with TNF-α (also known as cachectin), and since each induces similar biologic responses and binds to the same cellular receptor, both TNF-α and TNF-β are considered to be inhibited by compounds of the present invention and thus are herein referred to collectively as "TNF" unless specifically indicated otherwise.

This invention relates to a method for mediating or inhibiting the enzymatic activity or catalytic activity of PDE IV in a mammal in need thereof and for inhibiting the production of TNF in a mammal in need thereof, which comprises administering to said mammal an effective amount of a compound of Formula (i) or a pharmaceutically-acceptable salt thereof.

PDE IV inhibitors are useful in the treatment of a variety of allergic and inflammatory diseases, including: asthma, chronic bronchitis, chronic obstructive airways disease, atopic dermatitis, atopic eczema, urticaria, allergic rhinitis, allergic conjunctivitis, vernal conjunctivitis, inflammation of the eye, allergic responses in the eye, eosinophilic granuloma, psoriasis, Bechet's disease, erythematosis, anaphylactoid purpura nephritis, joint inflammation, arthritis, rheumatoid arthritis and other arthritic conditions such as rheumatoid spondylitis and osteoarthritis, septic shock, sepsis, ulcerative colitis, Crohn's disease, reperfusion injury of the myocardium and brain, chronic glomerulonephritis, endotoxic shock and adult respiratory distress syndrome. In addition, PDE IV inhibitors are useful in the treatment of diabetes insipidus and conditions associated with cerebral metabolic inhibition, such as cerebral senility, senile dementia (Alzheimer's disease), memory impairment associated with Parkinson's disease, depression and multi-infarot dementia. PDE IV inhibitors are also useful in conditions ameliorated by neuroprotectant activity, such as cardiac arrest, stroke and intermittent claudication. PDE IV inhibitors may also be useful in the treatment of tardive dyskinesia, ischaemia and Huntingdon's disease. Additionally, PDE IV inhibitors could have utility as gastroprotectants. A special embodiment of the therapeutic methods of the present invention is the treatment of asthma.

The viruses contemplated for treatment herein are those that produce TNF as a result of infection, or those which are sensitive to inhibition, such as by decreased replication, directly or indirectly, by the TNF inhibitors of Formula (i). Such viruses include, but are not limited to HIV-1, HIV-2 and HIV-3, cytomegalovirus (CMV), influenza, adenovirus and the Herpes group of viruses, such as, but not limited to, *Herpes zoster* and *Herpes simplex*.

This invention more specifically relates to a method of treating a mammal, afflicted with a human immunodeficiency virus (HIV), which comprises administering to such mammal an effective TNF inhibiting amount of a compound of formula (i) or a pharmaceutically-acceptable salt thereof.

The compounds of this invention may also be used in association with the veterinary treatment of animals, other than humans, in need of inhibition of TNF production. TNF medicated diseases for treatment, therapeutically or prophylactically, in animals include disease states such as those noted above, but in particular viral infections. Examples of such viruses include, but are not limited to feline immunodeficiency virus (FIV) or other retroviral infection such as equine infectious anaemia virus, caprine arthritis virus, visna virus, maedi virus and other lentiviruses.

The compounds of this invention are also useful in treating parasite, yeast and fungal infections, where such yeast and fungi are sensitive to upregulation by TNF or will elicit TNF production in vivo. A preferred disease state for treatment is fungal meningitis.

Compounds of the invention may also suppress neurogenic inflammation through elevation of cAMP in sensory neurones. They are, therefore, analgesic, anti-tussive and anti-hyperalgesic in inflammatory diseases associated with irritation and pain.

The compounds of formula (i) are preferably in pharmaceutically-acceptable form. By pharmaceutically-acceptable form is meant, inter alia, of a pharmaceutically-acceptable level of purity excluding normal pharmaceutical additives such as diluents and carriers, and including no material considered toxic at normal dosage levels. A pharmaceutically-acceptable level of purity will generally by at least 50% excluding normal pharmaceutical additives, preferably 75%, more preferably 90% and still more preferably 95%.

The invention further provides a process for the preparation of a compound of formula (i), in which $R_1$ etc, m and n are as defined above. It will be appreciated that functional groups such as amino, hydroxyl or carboxyl groups present in the various compounds described below, and which it is desired to retain, may need to be in protected forms before any reaction is initiated. In such instances, removal of the protecting group may be the final step in a particular reaction sequence. Suitable protecting groups for such functionality will be apparent to those skilled in the art. For specific details, see Protective Groups in Organic Synthesis, Wiley Interscience, TW Greene. Thus the process for preparing compounds of formula (i) in which $R_4$ contains an —OH comprises deprotecting (for example by hydrogenolysis or hydrolysis) a compound of formula (i) in which $R_4$ contains an appropriate —OP wherein P represents a suitable protecting group (e.g. benzyl or acetyl).

It will be appreciated that where a particular steroisomer of formula (i) is required, this may be obtained by conventional resolution techniques such as high performance liquid chromatography or the synthetic processes herein described may be performed using the appropriate homochiral starting material.

A process for the preparation of a compound of formula (i) wherein X is CO comprises reaction of an appropriate carboxylic acid of formula (ii) with a suitable amine of formula (iii)

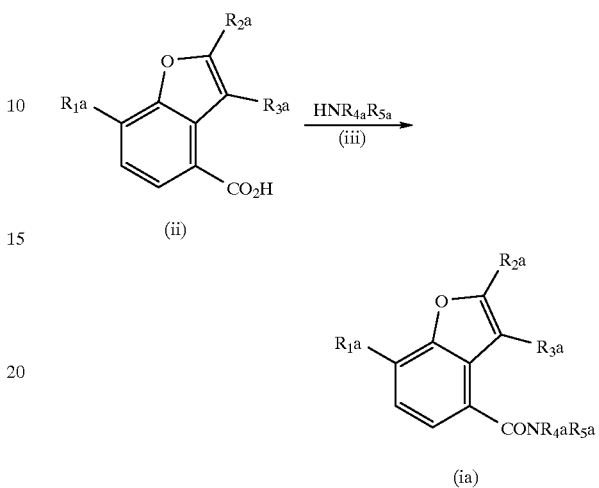

wherein $R_{1a}$ represents $R_1$ as defined in relation to formula (i) or a group convertible to $R_1$ and $R_{2a}$–$R_{5a}$, similarly represent $R_2$–$R_5$ or groups convertible to $R_2$–$R_5$ respectively; and thereafter, if required, converting any group $R_{1a}$ to $R_1$ and/or $R_{2a}$ to $R_2$ and/or $R_{3a}$ to $R_3$ and/or $R_{4a}$ to $R_4$ and/or $R_{5a}$ to $R_5$; and thereafter, if required, converting any group $R_{1a}$ to $R_1$ and/or $R_{2a}$ to $R_2$ and/or $R_{3a}$ to $R_3$ and/or $R_{4a}$ to $R_4$ and/or $R_{5a}$ to $R_5$. The reaction of a carboxylic acid of formula (ii) with an amine of formula (iii) may be carried out under any suitable conditions known to those skilled in the art. Preferably, the reaction is carried out in the presence of a suitable base, for example an amine such as triethylamine, preferably in an appropriate solvent such as dichloromethane. In some cases a stronger base, such as sodium hydride, and a polar solvent such as dimethylformamide, will be required. Preferably, the carboxylic acid is converted into an acid chloride, mixed anhydride or other activated intermediate prior to reaction with an amine of formula (iii).

Carboxylic acids of formula (ii) and amines of formula (iii) are either commercially available, previously described compounds or are prepared using standard procedures known to those skilled in the art. For example, a carboxylic acid of formula (ii) is conveniently prepared from an appropriate benzofuran of formula (v), using standard procedures known to those skilled in the art. For example, a benzofuran of formula (v) can be formulated to provide an aldehyde of formula (iv), which can then be oxidised to provide the corresponding acid of formula (ii). Alternatively, a benzofuran of formula (v) can be brominated to provide a bromide of formula (vi), which can then be converted into a carboxylic acid of formula (ii), for example by organometal-catalysed carboxylation, such as a palladium-catalysed reaction.

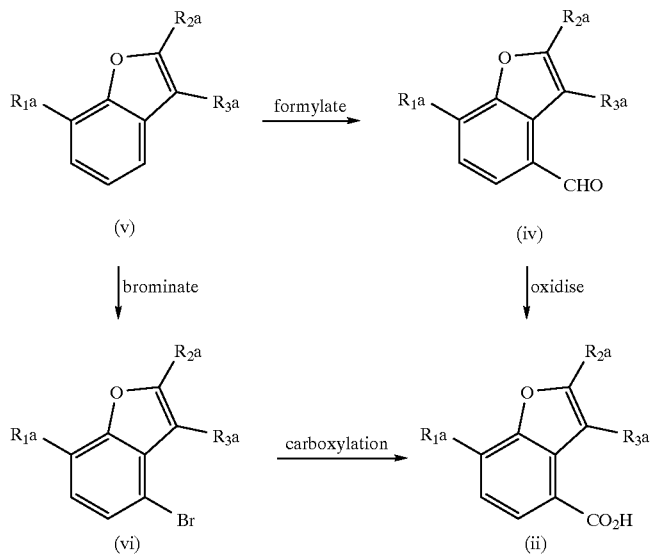

A compound of formula (ia) may also be prepared by reaction of a carboxylic acid of formula (ii) with an amine (iii) to provide a compound of formula (ia) in which $R_{4a}$ is H, followed by reaction with an agent $R_{4a}Y$ (vii) in which Y is a suitable leaving group such as a halogen. The first reaction can be carried out as described above. Preferably, the carboxylic acid is converted into an acid chloride, mixed anhydride or other activated intermediate prior to reaction with the amine (iii). The reaction with agent (vii) may be carried out under any suitable conditions known to those skilled in the art. It may be carried out in the presence of a suitable base, e.g. sodium hydride, preferably in an appropriate solvent such as dimethylformamide. Agents (vii) are known or commercially available, or are prepared using standard procedures known to those skilled in the art. Such compounds include alkylating agents such as propyl bromide, acylating agents such as benzoyl chloride and sulphonylating agents such as methanesulphonyl chloride.

Compounds of formula (i) may also be prepared by interconversion of other compounds of formula (i). For example, a compound in which $R_4$ contains an alkoxy group may be prepared by appropriate alkylation of a compound in which $R_4$ contains a hydroxy group. Compounds of formula (i) in which X is CS may be prepared from compounds of formula (i) in which X is CO using any appropriate conditions known to those skilled in the art, for example by using Lawesson's reagent.

By way of further example, compounds in which $R_2$ and/or $R_3$ contain an oxime may be prepared from compounds in which $R_2$ and/or $R_3$ contain a carbonyl group. This transformation may be carried out using any appropriate standard conditions known to those skilled in the art. Compounds of formula (i) in which $R_2$ and/or $R_3$ contain a carbonyl group may be reduced using standard conditions known to those skilled in the art (for example with sodium borohydride in an appropriate solvent) to provide compounds in which $R_2$ and/or $R_3$ contains an alcohol group. Other transformations may be carried out on compounds of formula (i) in which $R_2$ and/or $R_3$ contains a carbonyl group. Such transformations include, but are not limited to, reductive amination and alkylation. Compounds in which $R_2$ and/or $R_3$ contain an $COR_{15}$ group may be prepared from compounds in which $R_2$ and/or $R_3$ contain a CN group by addition of a suitable organometallic agent (such as a Grignard reagent). Any of the above transformations may be carried out either at the end of the synthesis or on an appropriate intermediate.

A compound of formula (i) or where appropriate a pharmaceutically-acceptable salt thereof and/or a pharmaceutically-acceptable solvate thereof, may be administered per se or, preferably, as a pharmaceutical composition also comprising a pharmaceutically-acceptable carrier.

Accordingly, the present invention provides a pharmaceutical composition comprising a compound of formula (i) or where appropriate a pharmaceutically-acceptable salt thereof and/or a pharmaceutically-acceptable solvate thereof, and a pharmaceutically-acceptable carrier.

The active compound may be formulated for administration by any suitable route, the preferred route depending upon the disorder for which treatment is required, and is preferably in unit dosage form or in a form that a human patient may administer to himself in a single dosage. Advantageously, the composition is suitable for oral, rectal, topical, parenteral administration or through the respiratory tract. Preparations may be designed to give slow release of the active ingredient.

The term parenteral as used herein includes subcutaneous injections, intravenous, intramuscular, intrasternal injection or infusion techniques. In addition to the treatment of warm-blooded animals such as mice, rats, horses, cattle, sheep, dogs, cats, etc, the compounds of the invention are effective in the treatment of humans.

The compositions of the invention may be in the form of tablets, capsules, sachets, vials, powders, granules, lozenges, suppositories, reconstitutable powders, or liquid preparations such as oral or sterile parenteral solutions or suspensions. Topical formulations are also envisaged where appropriate.

In order to obtain consistency of administration it is preferred that a composition of the invention is in the form of a unit dose.

Unit dose presentation forms for oral administration may be tablets and capsules and may contain conventional excipients such as binding agents, for example syrup, acacia, gelatin, sorbitol, tragacanth, or polyvinylpyrrolidone; fillers for example microcrystalline cellulose, lactose, sugar, maize-starch, calcium phosphate, sorbitol or glycine; tabletting lubricants, for example magnesium stearate; disintegrants, for example starch, polyvinylpyrrolidone, sodium starch glycollate or microcrystalline cellulose; or pharmaceutically-acceptable wetting agents such as sodium lauryl sulphate.

The solid oral compositions may be prepared by conventional methods of blending, filling, tabletting or the like. Repeated blending operations may be used to distribute the active agent throughout those compositions employing large quantities of fillers.

Such operations are of course conventional in the art. The tablets may be coated according to methods well known in normal pharmaceutical practice, in particular with an enteric coating.

Oral liquid preparations may be in the form of, for example, emulsions, syrups or elixirs, or may be presented as a dry product for reconstitution with water or other suitable vehicle before use. Such liquid preparations may contain conventional additives such as suspending agents, for example sorbitol, syrup, methyl cellulose, gelatin, hydroxyethylcellulose, carboxymethylcellulose, aluminium stearate gel, hydrogenated edible fats; emulsifying agents, for example lecithin, sorbitan monooleate, or acacia, non-aqueous vehicles (which may include edible oils), for example almond oil, fractionated coconut oil, oily esters such as esters of glycerine, propylene glycol, or ethyl alcohol; preservatives, for example methyl or propyl p-hydroxybenzoate or sorbic acid; and if desired conventional flavouring or colouring agents.

Compositions may also suitably be presented for administration to the respiratory tract as a snuff or an aerosol or solution for a nebuliser, or as a microfine powder for insufflation, alone or in combination with an inert carrier such as lactose. In such a case the particles of active compound suitably have diameters of less than 50 $\mu$m, such as from 0.1 to 50 $\mu$m, preferably less than 10 $\mu$m, for example from 1 to 10 $\mu$m, 1 to 5 $\mu$m or from 2 to 5 $\mu$m. Where appropriate, small amounts of other anti-asthamatics and bronchodilators for example sympathomimetic amines such as isoprenaline, isoetharine, salbutamol, phenylephrine and ephedrine, corticosteroids such as prednisolone and adrenal stimulants such as ACTH may be included.

For parenteral administration, fluid unit dosage forms are prepared utilizing the compound and a sterile vehicle, and, depending on the concentration used, can be either suspended or dissolved in the vehicle. In preparing solutions the compound can be dissolved in water for injection and filter sterilised before filling into a suitable vial or ampoule and sealing.

Advantageously, adjuvants such as local anaesthetic, a preservative and buffering agents can be dissolved in the vehicle. To enhance the stability, the composition can be frozen after filling into the vial and the water removed under vacuum. Parenteral suspensions are prepared in substantially the same manner, except that the compound is suspended in the vehicle instead of being dissolved, and sterilisation cannot be accomplished by filtration. The compound can be sterilised by exposure to ethylene oxide before suspending in the sterile vehicle. Advantageously, a surfactant or wetting agent is included in the composition to facilitate uniform distribution of the compound.

The compositions may contain from 0.1% to 99% by weight, preferably from 10–60% by weight, of the active material, depending on the method of administration.

Compounds of formula (i), or if appropriate a pharmaceutically-acceptable salt thereof and/or a pharmaceutically-acceptable solvate thereof, may also be administered as a topical formulation in combination with conventional topical excipients.

Topical formulations may be presented as, for instance, ointments, creams or lotions, impregnated dressings, gels, gel sticks, spray and aerosols, and may contain appropriate conventional additives such as preservatives, solvents to assist drug penetration and emollients in ointments and creams. The formulations may contain compatible conventional carriers, such as cream or ointment bases and ethanol or oleyl alcohol for lotions.

Suitable cream, lotion, gel, stick, ointment, spray or aerosol formulations that may be used for compounds of formula (i) or if appropriate a pharmaceutically-acceptable salt thereof, are conventional formulations well known in the art, for example, as described in standard text books such as Harry's Cosmeticology published by Leonard Hill Books, Remington's Pharmaceutical Sciences, and the British and US Pharmacopoeias.

Suitably, the compound of formula (i), or if appropriate a pharmaceutically-accceptable salt thereof, will comprise from about 0.5 to 20% by weight of the formulation, favourably from about 1 to 10%, for example 2 to 5%.

The dose of the compound used in the treatment of the invention will vary in the usual way with the seriousness of the disorders, the weight of the sufferer, and the relative efficacy of the compound. However, as a general guide suitable unit doses may be 0.1 to 1000 mg, such as 0.5 to 200, 0.5 to 100 or 0.5 to 10 mg, for example 0.5, 1, 2, 3, 4 or 5 mg; and such unit doses may be administered more than once a day, for example 2, 3, 4, 5 or 6 times a day, but preferably 1 or 2 times per day, so that the total daily dosage for a 70 kg adult is in the range of about 0.1 to 1000 mg, that is in the range of about 0.001 to 20 mg/kg/day, such as 0.007 to 3, 0.007 to 1.4, 0.007 to 0.14 or 0.01 to 0.5 mg/kg/day, for example 0.01, 0.02, 0.04, 0.05, 0.06, 0.08, 0.1 or 0.2 mg/kg/day, and such therapy may extend for a number of weeks or months.

When used herein the term "pharmaceutically-acceptable" encompasses materials suitable for both human and veterinary use.

The following Examples illustrate the invention.

INTERMEDIATE 1

2-Acetyl-7-methoxybenzofuran-4-carbonyl chloride

2-Acetyl-7-methoxybenzofuran-4-carboxylic acid (0.12 g) was suspended in anhydrous dichloromethane (4 ml) at room temperature under nitrogen and oxalyl chloride (0.1 ml) added followed by 3 drops of N,N-dimethylformamide. Evaporation in vacuo after 2 h afforded the title compound as a yellow solid (~0.5 g).

TLC $R_f$ 0.60 (50% ethyl acetate in hexane)

INTERMEDIATE 2

2-Acetyl-7-methoxybenzofuran-4-carboxylic acid

A mixture of 2-acetyl-4-bromo-7-methoxybenzofuran (5 g), triphenylphosphine (98 mg), bis(triphenylphosphine) palladium(II)chloride (261 mg), triethylamine (2.85 ml) and water (1 ml) in tetrahydrofuran (25 ml) was purged with carbon monoxide gas in a Parr pressure reactor at 110 psi. This was heated to 110° C. (pressure now 220 psi) and left for a week. On cooling and release of pressure the mixture was dissolved in 50% dichloromethane-water (200 ml) and taken to pH12 using aqueous sodium hydroxide (1M). The separated aqueous phase was acidified to pH1 using dilute hydrochloric acid (1M) and the resultant slurry extracted with dichloromethane (3×100 ml) then ethyl acetate (100 ml). These combined organic extracts were dried over magnesium sulphate, filtered and evaporated in vacuo to afford a yellow solid (2.58 g).
TLC $R_f$ 0.61 (ethyl acetate)

INTERMEDIATE 3

2-Acetyl-4-bromo-7-methoxybenzofuran

A solution of bromine (5.5 ml) in methanol (100 ml) was added dropwise to a suspension of 2-acetyl-7-methoxybenzofuran (20 g) in methanol (300 ml) at 0° C. The ice bath was removed immediately and the mixture allowed to warm to room temperature. After 1 h conversion was incomplete, so further bromine (0.75 ml) in methanol (25 ml) was added and the mixture stirred overnight. The reaction was quenched using aqueous sodium metabisulphite solution (300 ml) producing a precipitate that was filtered off and dried in vacuo to afford a brown solid (17.4 g).
TLC $R_f$ 0.90 (ethyl acetate)

INTERMEDIATE 4

2-(1-(t-Butyldimethylsilyloxy)iminoethyl)-7-methoxy-4-[N-3,5-dichloropyrid-4-yl]benzofuran carboxamide To a solution of 2-acetyl-7-methoxy-4-[N-(3,5-dichloropyrid-4-yl)]benzofuran carboxamide (0.5 g) in toluene (50 ml) was added O-(t-butyldimethylsilyl) hydroxylamine (0.39 g). The reaction mixture was heated under a nitrogen atmosphere under Dean Stark conditions for 3 days then left stirring at room temperature for 2 days. The reaction mixture was concentrated to dryness in vacuo giving the crude product. Purification by flash chromatography on silica eluting with 50% ethyl acetate in hexane afforded a white solid (0.22 g).
TLC $R_f$ 0.53 (50% ethyl acetate in hexane)

INTERMEDIATE 5

2-[(Pyridin-4-yl)carbonyl]-7-methoxybenzofuran-4-carbonyl chloride hydrochloride The title compound was prepared in a similar manner to Intermediate 1.

INTERMEDIATE 6

2-[(Pyridin-4-yl)carbonyl]-7-methoxybenzofuran-4-carboxylic acid

2-[(Pyridin-4-yl)carbonyl]-4-bromo-7-methoxybenzofuran (3.3 g), triphenylphosphine (1 g), bis(triphenylphosphine)palladium(II)chloride (0.47 g), triethylamine (14 ml), tetrahydrofuran (150 ml) and water (57 ml) were combined in a Parr pressure reactor. The vessel was purged with carbon monoxide, charged to 180 psi with carbon monoxide and then heated to 80° C. with stirring for 3 days. On cooling and release of pressure the tetrahydrofuran was removed in vacuo. The remaining aqueous mixture was basified to pH14 with 1N sodium hydroxide solution (250 ml) and washed with ethyl acetate (200 ml). The aqueous layer was then acidified to pH5 with acetic acid under ice bath cooling. The resulting precipitate was collected by filtration and dried to give a beige solid (2.97 g).
M.S. M+H observed

INTERMEDIATE 7

2-[(Pyridin-4-yl)carbonyl]-4-bromo-7-methoxybenzofuran

Bromine (0.02 ml) was added to a mixture of 2-[(pyridin-4-yl)carbonyl]-7-methoxy benzofuran (0.1 g) in methanol (7 ml) under a nitrogen atmosphere cooled to −78° C. The reaction mixture was allowed to warm to room temperature over 2.5 h. The reaction was then diluted with ethyl acetate (40 ml), washed with 5% sodium metabisulfite solution (2×20 ml), saturated sodium bicarbonate solution (40 ml), dried over magnesium sulphate and concentrated to dryness in vacuo to afford a pale yellow solid (0.05 g) as a 2:1 mixture of product:starting material by nmr.
TLC $R_f$ 0.65 (10% methanol in ethyl acetate)

INTERMEDIATE 8

2-[(Pyridin-4-yl)carbonyl]-7-methoxybenzofuran

Sodium hydroxide (1.22 g) was added to a solution of o-vanillin (2.11 g) in ethanol (50 ml) at 55° C. under a nitrogen atmosphere. The reaction mixture was stirred for 10 minutes to give a yellow suspension. 4-(Bromoacetyl)pyridine hydrobromide (5 g) was then added portionwise and the solution heated at 55° C. for 12 h, then at 65–70° C. for a further 12 h. The reaction mixture was cooled to room temperature and the solvent removed in vacuo. The residue was partitioned between water (250 ml, containing sodium hydroxide (0.5 g)) and dichloromethane (2×200 ml). The combined organic phases were washed with water (100 ml), dried over magnesium sulphate, filtered and evaporated in vacuo onto silica gel. The compound was washed through a pad of silica with ethyl acetate; the ethyl acetate was removed in vacuo and the residue azeotroped with hexane. The resulting solid was washed with hexane and filtered to furnish the title compound (0.95 g) as a yellow solid.
TLC $R_f$ 0.53 (ethyl acetate)

INTERMEDIATE 9

4-(Bromoacetyl)pyridine hydrobromide

4-Acetylpyridine (10 g) was combined with 48% hydrogen bromide solution (18 ml) and heated to 70° C. Bromine (4.7 ml) dissolved in 48% hydrogen bromide solution (5 ml) was then added dropwise and heating then continued for 2.5 h. The precipitate which had formed was collected by filtration, washed with 1:1 methanol:hexane (20 ml) and dried to give a cream solid (19.5 g) as a 2:1 mixture of product:starting material by $^1$H nmr.
mp 170–172° C.

INTERMEDIATE 10

2-Acetyl-7-methoxy-4-[N-(3,5-dichloropyrid-4-yl)]benzofuran carboxamide

Sodium hydride (0.03 g) was added to a solution of 4-amino-3,5-dichloropyridine (0.08 g) in anhydrous N,N-dimethylformamide (1 ml) at room temperature under nitrogen. This stirred mixture was warmed to 60° C. for 1 h before addition of 2-acetyl-7-methoxybenzofuran-4-carbonylchloride (generated from 2-acetyl-7-methoxybenzofuran-4-carboxylic acid, 0.12 g) washed in with anhydrous N,N-dimethylformamide (2 ml). The brown mixture was heated at 60° C. for 4 h, allowed to cool, poured into water (100 ml) and extracted into ethyl acetate (2×50 ml). These organic extracts were washed with water (50 ml)

and saturated brine (50 ml) then dried over magnesium sulphate, filtered and evaporated in vacuo to give a crude residue (0.17 g). Purification by column chromatography on silica eluting with a 20–80% ethyl acetate in hexane gradient afforded a white solid (0.04 g).
TLC $R_f$ 0.20 (50% ethyl acetate in hexane)
mp 252–254° C.

INTERMEDIATE 11

2-[(Pyridin-4-yl)carbonyl]-7-methoxybenzofuran-4-[N-(3,5-dichloropyridin-4-yl]carboxamide Sodium hydride (0.3 g) was added to a solution of 4-amino-3,5-dichloropyridine (0.56 g) in dimethylformamide (10 ml) under an atmosphere of nitrogen. The reaction mixture was heated to 55° C. for 1 hr then 2-[(pyridin-4-yl)carbonyl]-7-methoxybenzofuran-4-carbonyl chloride was added in one portion. Heating at 55° C. was continued for 2 h then at room temperature for 12 h. The reaction mixture was concentrated to dryness in vacuo to give the crude product. Purification by flash chromatography on silica eluting with ethyl acetate and then 20% methanol in ethyl acetate afforded a cream solid (0.3 g).
TLC $R_f$ 0.36 (ethyl acetate)
mp 250–252° C.

INTERMEDIATE 12 t-Butyl-2-acetyl-7-methoxybenzofuran-4-carboxylate

A solution of 2-acetyl-7-methoxybenzofuran-4-carboxylic acid (100 mg) in dichloromethane (4 ml) was stirred at room temperature under an atmosphere of nitrogen. t-Butyl-2,2,2-trichloroacetimidate (0.16 ml) followed by boron trifluoride etherate (0.012 ml) were added and the mixture stirred at room temperature for 2 h. The reaction was quenched by the addition of a saturated solution of sodium bicarbonate (1 ml). The mixture was extracted with dichloromethane (3×10 ml) and the combined organic phases dried over magnesium sulphate. Removal of the solvent in vacuo and purification by flash chromatography eluting with dichloromethane gave the product as a white solid (130 mg).
TLC $R_f$ 0.25 (dichloromethane)

INTERMEDIATE 13

(Z)-t-Butyl-2-(t-methoxyiminoethyl)-7-methoxybenzofuran-4-carboxylate

A mixture of (Z)-t-butyl 2-acetyl-7-methoxybenzofuran-4-carboxylate (0.54 g), methoxylamine (0.31 g), pyridine (0.46 ml) and toluene (50 ml) was refluxed under Dean and Stark conditions overnight. The mixture was then cooled and the toluene removed in vacuo. The residue was taken up in ethyl acetate (100 ml) and washed with water (50 ml) then brine (50 ml). Drying over magnesium sulphate followed by removal of the solvent in vacuo and purification by flash chromatography eluting with dichloromethane gave the product as a colourless oil.
TLC $R_f$ 0.52 (dichloromethane)

INTERMEDIATE 14

(Z)-2-(1-Methoxyiminoethyl)-7-methoxybenzofuran-4-carboxylic acid

A solution of (Z)-t-butyl 2-(1-methoxyiminoethyl)-7-methoxybenzofuran-4-carboxylate (100 mg) and trifluoroacetic acid (0.05 ml) in dichloromethane (5 ml) was stirred at room temperature for 4 h. A further aliquot of trifluoroacetic acid (0.1 ml) was added and stirring continued overnight. The solvent was removed in vacuo and the residue was evapourated in vacuo from toluene (2×5 ml) and dichloromethane (2×5 ml) to remove excess trifluoroacetic acid. The product was obtained as a white solid (72 mg).
TLC $R_f$ 0.22 (dichloromethane)
mp 233–234° C.

INTERMEDIATE 15

(Z)-4-Nitrophenyl 2-(t-methoxyiminoethyl)-7-methoxybenzofuran-4-carboxylate

A solution of (Z)-2-(1-methoxyiminoethyl)-7-methoxybenzofuran-4-carboxylic acid (70 mg), 4-nitrophenol (41 mg), 1-(3-dimethylaminopropyl)-3-ethylcarbodiimide hydrochloride (56 mg) and 4-dimethylaminopyridine (catalytic) in dichloromethane (20 ml) was stirred at room temperature for 6 h under an atmosphere of nitrogen. The reaction mixture was diluted with dichloromethane (20 ml) and washed with water (3×20 ml). Drying over magnesium sulphate followed by concentration to dryness in vacuo gave a pale yellow solid. Purification by flash chromatography eluting with dichloromethane gave the product as a white solid (53 mg).
TLC $R_f$ 0.42 (dichloromethane)
mp 195–196° C.

EXAMPLE 1

2-(1-Hydroxyethyl)-7-methoxy-4-[N-(3,5-dichloropyrid-4-yl)]benzofurancarboxamide 2-Acetyl-7-methoxy-4-[N-(3,5-dichloropyrid-4-yl)]benzofurancarboxamide (0.50 g) was suspended in dry methanol (20 ml) and treated with sodium borohydride (196 mg) at ambient temperature. Some external ice cooling was required, then the reaction mixture was stirred overnight. The reaction mixture was poured into water and extracted into ethyl acetate. Evaporation in vacuo yielded a solid that was purified by column chromatography using 5% methanol in dichloromethane to afford a white solid (400 mg).
TLC $R_f$ 0.52 (80% ethyl acetate in heptane)
mp 229–231° C.

EXAMPLE 2

2-(3-Pyrid-3-yl-1-oxopropyl)-7-methoxy-4-[N-(3,5-dichloropyrid-4-yl)]benzofurancarboxamide A solution of 2-acetyl-7-methoxy-4-[N-(3,5-dichloropyrid-4-yl)]benzofuran carboxamide (0.40 g) in dry N,N-dimethylformamide (5 ml) was cooled to −10° C. under an inert atmosphere and sodium hydride (60% dispersion in oil, 0.11 g) was added over 30 minutes. After 1 h at −10° C., 3-picolyl chloride hydrochloride (0.20 g) was added and the mixture stirred for a further 2 h before allowing to warm to room temperature overnight. It was poured into water and extracted into ethyl acetate. These extracts were washed with water and saturated brine then dried over anhydrous magnesium sulphate, filtered and evaporated in vacuo. The residue was purified by column chromatography using a 3–10% methanol in dichloromethane gradient. The product was triturated with diethyl ether to yield a beige powder (15 mg).
TLC $R_f$ 0.27 (10% methanol in dichloromethane).

EXAMPLE 3

2-(t-Benzyloxyimino)ethyl-7-methoxy-4-[N-(3,5-dichloropyrid-4-yl)]benzofurancarboxamide 2-Acetyl-7-methoxy-4-[N-(3,5-dichloropyrid-4-yl)]benzofurancarboxamide (100 mg) was refluxed under Dean- Stark conditions in dry toluene (40 ml) with dry pyridine (64 μl) and O-benzylhydroxylamine hydrochloride (126 mg) under an inert atmosphere. After 2 h the mixture was allowed to cool and left stirring overnight. Addition of methanol and acetone formed a precipitate. This was filtered off to afford a solid (26 mg).
TLC $R_f$ 0.45 (50% ethyl acetate in hexane).

EXAMPLE 4

2-(t-Methoxyiminoethyl)-7-methoxy-4-[N-(3,5-dichloropyrid-4-yl)]benzofurancarboxamide To a suspension of 2-acetyl-7-methoxy-4-[N-(3,5-dichloropyrid-4-yl)]benzofuran carboxamide (0.07 g) in dry toluene (40 ml) was added pyridine (0.09 ml) and methoxylamine hydrochloride (0.056 g) and the mixture heated under Dean-Stark conditions for 24 h. Evaporation of the solvent and purification by flash chromatography on silica eluting with dichloromethane then 5% methanol in dichloromethane followed by preparative tlc (5% methanol in dichloromethane) afforded a white solid (0.03 g) as a mixture of E and Z isomers by $^1$H nmr.
TLC $R_f$ 0.27–0.34 (50% ethyl acetate in hexane)

EXAMPLE 5

2-[2-(4-Morpholino)-(2-methoxy)iminoethyl]-7-methoxy-4-[N-(3,5-dichloropyrid-4-yl)]benzofurancarboxamide Prepared from 2-(4-morpholino)acetyl-7-methoxy-4-[N-(3,5-dichloropyrid-4-yl)]benzofurancarboxamide by a similar procedure to that of Example 4. Purification by flash chromatography on silica eluting with ethyl acetate afforded the product as a yellow solid as a 1:1 mixture of isomers (20 mg).
TLC $R_f$ 0.66 and 0.53 (ethyl acetate)
mp 140° C. (dec.)

EXAMPLE 6

Z-2-(1-Hydroxyiminoethyl)-7-methoxy-4-[N-(3,5-dichloropyridin-4-yl)]benzofurancarboxamide To a suspension of 2-acetyl-7-methoxy-4-[N-(3,5-dichloropyrid-4-yl)]benzofuran carboxamide (0.5 g) in dry toluene (30 ml) was added pyridine (1 g) and hydroxylamine (0.9 g) and the mixture heated under Dean-Stark conditions for 48 h. Evaporation of the solvent in vacuo and washing the product was water afforded an off white solid (0.2 g)
TLC $R_f$ 0.22 (50% ethyl acetate in hexane)
mp 250° C. (dec)

EXAMPLE 7

Z-2-(1-Hydroxyiminoethyl)-7-methoxy-4-[N-methyl-N-(3,5-dichloropyridin-4-yl)]benzofurancarboxamide To a solution of Z-2-(1-hydroxyiminoethyl)-7-methoxy-4-[N-(3,5-dichloropyridin-4-yl)]benzofurancarboxamide (50 mg) in tetrahydrofuran (10 ml) was added tetrabutylammonium iodide (cat. amount) followed by a solution of sodium hydroxide (6 mg) in water (1 ml). The whole was stirred for 20 mins then methyl iodide (45 mg) was added and stirring continued for 12 hrs. The mixture was concentrated to dryness, diluted with ethyl acetate (20 ml), washed with water (10 ml), brine (10 ml), dried over magnesium sulphate and concentrated by dryness again giving the crude product. Purification by flash chromatography on silica eluting with 50% ethyl acetate in hexane afforded a white solid (24 mg).
TLC $R_f$ 0.37 (50% ethyl acetate in hexane)
mp 97–98° C.

EXAMPLE 8

Z-2-(1-(4-Pyridylmethoxy)iminoethyl)-7-methoxy-4-[N-(3,5-dichloropyrid-4-yl)]benzofurancarboxamide To a solution of Z-2-(1-hydroxyiminoethyl)-7-methoxy-4-[N-(3,5-dichloropyridin-4-yl)]benzofurancarboxamide (50 mg) in tetrahydrofuran (10 ml) was added tetrabutylammonium iodide (cat. amount) followed by a solution of sodium hydroxide (17 mg) in water (1 ml). The whole was stirred for 20 mins then 4-chloromethylpyridine hydrochloride (46 mg) was added and stirring continued for 48 h. The mixture was concentrated to dryness, diluted with ethyl acetate (20 ml), washed with water (10 ml), brine (10 ml), dried over magnesium sulphate and concentrated to dryness again giving the crude product. Purification by flash chromatography on silica eluting with 50% ethyl acetate in hexane afforded an off white solid (10 mg).
TLC $R_f$ 0.26 (ethyl acetate)
mp 217–218° C.

EXAMPLE 9

E-2-(1-Hydroxyiminoethyl)-7-methoxy-4-[N-(3,5-dichloropyridin-4-yl)]benzofurancarboxamide Tetrabutylammonium fluoride (1M solution in tetrahydrofuran) (0.48 ml) was added to a solution of 2-(1-(t-butyldimethylsilyloxy)iminoethyl)-7-methoxy-4-[N-3,5-dichloropyrid-4-yl]benzofurancarboxamide in tetrahydrofuran (10 ml) under a nitrogen atmosphere. Stirring was continued for 20 minutes then the reaction mixture was concentrated to dryness in vacuo giving the crude product. Purification by flash chromatography on silica eluting with 50% ethyl acetate in hexane afforded an off white solid (0.1 g) as a 2:1 mixture of E:Z isomers by $^1$H nmr.
TLC $R_f$ 0.22 (50% ethyl acetate in hexane)
mp 280° C. (dec.)

EXAMPLE 10

2-[Methoxyimino(4-pyridyl)methyl]-7-methoxy-4-[N-(3,5-dichloropyridin-4-yl]benzofurancarboxamide 2-[(Pyridin-4-yl)carbonyl]-7-methoxy-4-[N-(3,5-dichloropyridin-4-yl]benzofuran carboxamide (0.25 g) was treated with methoxylamine hydrochloride (0.165 g) as in Example 4. The crude product was washed with water and then diethyl ether to give a white solid (0.217 g) as a 5.5:4.5 mixture of E:Z isomers by $^1$H nmr.
mp 245–247° C.
M.S. [M+H] observed

EXAMPLE 11

E-2-(1-(4-Pyridylmethoxy)iminoethyl)-7-methoxy-4-[N-(3,5-dichloropyrid-4-yl)]benzofurancarboxamide Sodium (9 mg) was added to a suspension of Z-2-(1-hydroxyiminoethyl)-7-methoxy-4-[N-(3,5-dichloropyridin-4-yl)]benzofurancarboxamide (50 mg) in ethanol (2 ml) under a nitrogen atmosphere. When all the solids dissolved, 4-chloromethylpyridine hydrochloride (21 mg) was added and the reaction mixture was stirred at room temperature for 3 days. More sodium (6 mg) and 4-chloromethylpyridine hydrochloride (21 mg) were added and the reaction mixture was heated to 85° C. for 6 h. The reaction was quenched with water (20 ml), extracted with ethyl acetate (3×20 ml). The combined organic layers were washed with water (20 ml), brine (20 ml), dried over magnesium sulphate and concentrated to dryness in vacuo to give the crude product. Purification by flash chromatography on silica eluting with ethyl acetate afforded on off white solid (18 mg).
TLC $R_f$ 0.43 (ethyl acetate)
mp 231–232° C.

EXAMPLE 12

2-(4-Morpholine)acetyl-7-methoxy-4-[N-(3,5-dichloropyrid-4-yl)]benzofuran carboxamide Bromine (0.01 ml) was added to a solution of 2-acetyl-7-methoxy-4-[N-(3,5-dichloro pyridin-4-yl)]benzofurancarboxamide (0.1 g) in 45% hydrogen bromide/acetic acid (4 ml) under an atmosphere of nitrogen. The reaction mixture was stirred at room temperature for 12 h then quenched with water (20 ml) and extracted with ethyl acetate (3×20 ml). The combined organic layers were washed with saturated aqueous sodium bicarbonate (20 ml), brine (20 ml), dried over magnesium sulphate and concentrated to dryness in vacuo to give the crude 2-bromoacetyl-7-methoxy-4-[N-(3,5-dichloropyrid-4-yl)]benzofuran carboxamide. Purification by flash chromatography on silica eluting with 50% ethyl acetate in hexane afforded an impure yellow solid (20 mg) which was used without further purification.

Morpholine (0.09 ml) and triethylamine (10 mg) were added to a solution of 2-bromoacetyl-7-methoxy-4-[N-(3,5-dichloropyrid-4-yl)]benzofurancarboxamide (20 mg) in dichloromethane (5 ml) under a nitrogen atmosphere. Stirring was continued for 1.5 h. The reaction mixture was then diluted with more dichloromethane washed with water, dried over magnesium sulphate and concentrated to dryness in vacuo to give the crude product. Purification by flash chromatography on silica eluting with ethyl acetate afforded a yellow solid (10 mg).
TLC $R_f$ 0.38 (ethyl acetate)
mp 130° C. (dec.)

EXAMPLE 13

(Z)-2-[1-(2-Methylthiazol-4-ylmethoxy)iminoethyl]-7-methoxy-4-[N-(3,5-dichloropyrid-4-yl)]benzofurancarboxamide A solution of (Z)-2-(1-hydroxyiminoethyl)-7-methoxy-4-[N-(3,5-dichloropyridin-4-yl)]benzofurancarboxamide (0.75 g) in dimethylformamide (30 ml) was stirred at room temperature under an atmosphere of nitrogen. Sodium hydride (60% dispersion in oil) (0.17 g) was added and stirring continued for 1 h. 4-Chloromethyl-2-methylthiazole (0.84 g) was added (generated from the hydrochloride salt using sodium bicarbonate) and the mixture stirred for 1 h. The mixture was poured onto water (100 ml) and extracted with ethyl acetate (3×100 ml). The combined organic washings were washed with water (100 ml) and brine (50 ml), dried over magnesium sulphate and the solvent removed in vacuo to give creamy solid. The solid was triturated with ether to removed unreacted alkylating agent and purified by flash chromatography eluting with 0–10% methanol in ethyl acetate to give the product as a white solid (0.69 g).
TLC $R_f$ 0.62 (ethyl acetate)
mp 221–222° C.

The following Example was prepared by a similar procedure.

EXAMPLE 14

(Z)-2-(1-(4-Morpholinoethoxy)iminoethyl)-7-methoxy-4-[N-(3,5-dichloropyrid-4-yl)]benzofurancarboxamide Purification by recrystallisation from ethyl acetate/hexane gave the produce as a white solid (0.22 g)
TLC $R_f$ 0.50 (10% methanol in dichloromethane)
mp 178–179° C.

EXAMPLE 15

(Z)-2-(1-Methoxyiminoethyl)-7-methoxy-4-[N-(3,5-dichloropyrid-4-yl)]benzofurancarboxamide A solution of 4-amino-3,5-dichloropyridine (23 mg) in dimethylformamide (5 ml) was stirred at room temperature under an atmosphere of nitrogen. Sodium hydride (60% dispersion in oil) (9 mg) was added and the resulting suspension stirred for 1 h. A solution of 4-nitrophenyl 2-(1-methoxyiminoethyl)]-7-methoxybenzofuran-4-carboxylate (50 mg) in dimethylformamide (2 ml) was added and stirring continued overnight. The reaction was quenched by the addition of water (1 ml) and the mixture concentrated to dryness in vacuo. Purification by flash chromatography eluting with 50% ethyl acetate in hexane gave the produce as a white solid (23 mg).
TLC $R_f$ 0.40 (50% ethyl acetate in hexane)
mp 238–239° C.

ASSAY METHODS

The assays used to confirm the phosphodiesterase IV inhibitory activity of compounds of formula (i) are standard assay procedures as disclosed by Schilling et al, Anal. Biochem. 216:154 (1994), Thompson and Strada, Adv. Cycl. Nucl. Res. 8:119 (1979) and Gristwood and Owen, Br. J. Pharmacol. 87:91P (1986).

Compounds of formula (i) have exhibited activity at levels consistent with those believed to be useful in treating phosphodiesterase IV-related disease states in those assays.

In particular, the compound of Example 2 exhibits an activity of 6 nM using the assay procedure described by Gristwood and Owen. In comparison, 2-[1-(2,2-dimethylpropyl)]-7-methoxy-4-N-(3,5-dichloropyrid-4-yl) benzofurancarboxamide, within the scope of the claims of EP-A-0771794 (cf. Example 36 therein), exhibits an activity of 1.6 mM using the same assay procedure.

The ability of compounds of formula (i) to inhibit TNF production in human peripheral blood mononuclear cells (PMBC's) is measured as follows. PMBC's are prepared from freshly taken blood or "buffy coats" by standard procedures. Cells are plated out in RPMI1640+1% foetal calf serum in the presence and absence of inhibitors. LPS (100 ng/ml) is added and cultures are incubated for 22 h at 37° C. in an atmosphere of 95% air/5% $CO_2$. Supernatants are tested for TNFα by ELISA using commercially available kits.

In vivo activity in a skin eosinophilia model is determined by using the methods described by Hellewell et al, Br. J. Pharmacol. 111:811 (1994) and Br. J. Pharmacol. 110:416 (1993). Activity in a lung model is measured using the procedures described by Kallos and Kallos, Int. Archs. Allergy Appl. Immunol. 73:77 (1984), and Sanjar et al, Br. J. Pharmacol. 99:679 (1990).

An additional lung model, which allows measurement of inhibition of the early and late-phase asthmatic responses and also the inhibition of airway hyperactivity, is described by Broadley et al, Pulmonary Pharmacol. 7:311 (1994), J. Immunological Methods 190:51 (1996) and British J. Pharmacol. 116:2351 (1995). Compounds of the invention show activity in this model.

ABBREVIATIONS

LPS Lipopolysaccharide (endotoxin)
ELISA Enzyme linked immunosorbent assay

We claim:

1. A compound of the formula (i)

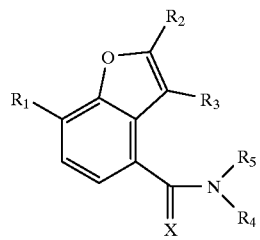

(i)

wherein $R_1$ is selected from the group consisting of alkoxy (optionally substituted with one or more halogens), OH, and thioalkyl;

$R_2$ and $R_3$, which may be the same or different, are each selected from the group consisting of H, halogen, $OR_{10}$, $CF_3$, $C(=NOR_6)R_6$, alkyl-$C(=NOR_6)R_6$, $COR_{15}$, $NR_8R_9$, heterocyclo optionally substituted with $R_{14}$, heterocycloalkyl optionally substituted with $R_{14}$, heteroarylalkyl optionally substituted with $R_{14}$, alkyl substituted with $R_{16}$, and cycloalkyl substituted with $R_{14}$, with the proviso that $R_2$ is not H;

$R_4$ is selected from the group consisting of H; arylalkyl, heteroarylalkyl, heterocycloalkyl, $S(O)_mR_{10}$, and alkyl optionally substituted with one or more substituents selected from the group consisting of hydroxy, alkoxy, $CO_2R_7$, $SO_2NR_{11}R_{12}$, $CONR_{11}R_2$, —CN, carbonyl oxygen $NR_8R_9$, $COR_{10}$, and $S(O)_nR_{10}$;

$R_5$ is selected from the group consisting of aryl, heteroaryl, heterocyclo, heteroarylalkyl, and heterocycloalkyl;

for $R_4$ and/or $R_5$, the aryl/heteroaryl/heterocyclo portion may be optionally substituted with one or more substituents alkyl-$R_{13}$ or $R_{13}$;

$R_6$ is selected from the group consisting of H and $R_{10}$ optionally substituted at any position with one or more $R_{14}$;

$R_7$ is selected from the group consisting of H, alkyl, arylalkyl, heteroarylalkyl, and heterocycloalkyl;

$R_8$ is selected from the group consisting of H, aryl, heteroaryl, heterocyclo, alkyl, arylalkyl, heteroarylalkyl, heterocycloalkyl, alkylcarbonyl, alkoxycarbonyl, arylsulphonyl, heteroarylsulphonyl, heterocyclosulphonyl, arylcarbonyl, heteroarylcarbonyl, heterocyclocarbonyl, and alkylsulphonyl;

$R_{10}$ is selected from the group consisting of alkyl, cycloalkyl, aryl, heteroaryl, heterocyclo, arylalkyl, heteroarylalkyl, and heterocycloalkyl;

$R_9$, $R_{11}$, and $R_{12}$, which may be the same or different, are each selected from the group consisting of H and $R_{10}$;

$R_{13}$ is selected from the group consisting of alkyl and alkoxy optionally substituted by a substituent selected from the group consisting of halogen, aryl, heteroaryl, heterocyclo, hydroxy, aryloxy, heteroaryloxy, heterocyclooxy, arylalkyloxy, heteroarylalkyloxy, heterocycloalkyloxy, $CO_2R_7$, $CONR_{11}R_{12}$, $SO_2NR_{11}R_{12}$, halogen, —CN, —$NR_8R_9$, $COR_{10}$, $S(O)_nR_{10}$, and carbonyl oxygen;

$R_{14}$ is selected from the group consisting of alkyl, hydroxy, $OR_{10}$, carbonyl oxygen, $NR_8R_9$, CN, $CO_2H$, $CO_2R_{10}$, $CONR_{11}R_{12}$, and $COR_{10}$;

$R_{15}$ is selected from the group consisting of heteroarylalkyl optionally substituted with $R_{14}$, heterocycloalkyl optionally substituted with $R_{14}$, aryl optionally substituted with $R_{14}$, heterocyclo (not attached through nitrogen) optionally substituted with $R_{14}$, alkyl substituted with $R_{14}$ and cycloalkyl substituted with $R_{14}$; with the proviso that when $R_{15}$ is alkyl substituted with $R_{14}$, then $R_{14}$ is not alkyl;

$R_{16}$ is selected from the group consisting of OH, $OR_{10}$, $NR_8R_9$, CN, and $COR_{15}$;

m=1–2;

n=0–2; and

X=O or S;

or a pharmaceutically acceptable salt thereof.

2. The compound, according to claim 1, wherein $R_1$ is alkoxy optionally substituted with one or more halogen.

3. The compound, according to claim 2, wherein

X is O;

$R_2$ and $R_3$ are the same or different and are each selected from the group consisting of H, $COR_{15}$, alkyl substituted with $R_{16}$ and cycloalkyl substituted with $R_{14}$;

$R_{13}$ is selected from the group consisting of aryl, heteroaryl, heterocyclo, hydroxy, alkoxy, aryloxy, heteroaryloxy, heterocyclooxy, arylalkoxy, heteroarylalkyloxy, heterocycloalkyloxy, $CO_2R_7$, $CONR_{11}R_{12}$; $SO_2NR_{11}R_{12}$, halogen, CN, $NR_8R_9$, $COR_{10}$, $S(O)_nR_{10}$, and carbonyl oxygen.

4. The compound, according to claim 1, wherein $R_4$ is selected from the group consisting of H and alkyl.

5. The compound, according to claim 1, wherein $R_5$ is selected from the group consisting of aryl and heteroaryl, which group is optionally substituted with one or more substituents $R_{13}$ or alkyl-$R_{13}$.

6. The compound, according to claim 1, wherein $R_2$ and $R_3$ are independently selected from the group consisting of H, $COR_{15}$, $C(=NOR_6)R_6$, heterocyclo optionally substituted with $R_{14}$, heterocycloalkyl optionally substituted with $R_{14}$, heteroarylalkyl optionally substituted with $R_{14}$, alkyl substituted with $R_{16}$, and cycloalkyl substituted with $R_{16}$, provided that $R_2$ is not H.

7. The compound, according to claim 2, wherein $R_2$ and $R_3$ are independently selected from the group consisting of heterocyclo optionally substituted with $R_{14}$, heterocycloalkyl optionally substituted with $R_{14}$, heteroarylalkyl optionally substituted with $R_{14}$, alkyl substituted with $R_{16}$, and cycloalkyl substituted with $R_{16}$, provided that $R_2$ is not H, wherein $R_{16}$ is selected from the group consisting of OH, $OR_{10}$, $NR_8R_9$, and $COR_{15}$, and $R_8$ and $R_9$ are independently selected from the group consisting of H and alkyl.

8. The compound, according to claim 1, which is selected from the group consisting of 2-(1-hydroxyethyl)-7-methoxy-4-[N-(3,5-dichloropyrid-4-yl)]benzofuran-carboxamide;

2-[3-(pyrid-3-yl)-1-oxopropyl]-7-methoxy-4-[N-(3,5-dichloropyrid-4-yl)]benzofurancarboxamide; and 2-(1-benzyloxyimino)ethyl-7-methoxy-4-[N-(3,5-dichloropyrid-4-yl)]benzofurancarboxamide.

9. The compound, according to claim 1, which is selected from the group consisting of 2-(1-methoxyiminoethyl)-7-methoxy-4-[N-(3,5-dichloropyrid-4-yl)]benzofurancarboxamide;

Z-2-(1-hydroxyiminoethyl)-7-methoxy-4-[N-(3,5-dichloropyridin-4-yl)]benzofurancarboxamide;

Z-2-(1-hydroxyiminoethyl)-7-methoxy-4-[N-methyl-N-(3,5-dichloropyridin-4-yl)]benzofurancarboxamide;

Z-2-[1-(4-pyridylmethoxy)iminoethyl]-7-methoxy-4-[N-(3,5-dichloropyrid-4-yl)]benzofurancarboxamide;

2-(1-hydroxyiminoethyl)-7-methoxy-4-[N-(3,5-dichloropyridin-4-yl)]benzofurancarboxamide;

2-[methoxyimino(4-pyridyl)methyl]-7-methoxy-4-[N-(3,5-dichloropyridin-4-yl]benzofurancarboxamide;

E-2-(1-(4-pyridylmethoxy)iminoethyl)7-methoxy-4-[N-(3,5-dichloropyrid-4-yl)]benzofurancarboxamide; and 2-(4-morpholino)acetyl-7-methoxy-4-[N-(3,5-dichloropyrid-4-yl)]benzofurancarboxamide.

10. The compound, according to claim 1, which is selected from the group consisting of 2-[2-[4-morpholino)-(2-methoxy)iminoethyl]-7-methoxy-4-[N-(3,5-dichloropyrid-4-yl)]benzofurancarboxamide;

(Z)-2-[1-(2-methylthiazol-4-ylmethoxy)iminoethyl]-7-methoxy-4-[N-(3,5-dichloropyrid-4-yl)]benzofurancarboxamide;

(Z)-2-(1-(4-morpholinoethoxy)iminoethyl)-7-methoxy-4-[N-(3,5-dichloropyrid-4-yl)]benzofurancarboxamide; and (Z)-2-(1-methoxyiminoethyl)-7-methoxy-4-[N-(3,5-dichloropyrid-4-yl)]benzofurancarboxamide.

11. The compound, according to claim 1, in the form of an enantiomer or mixture of enantiomers.

12. A pharmaceutical composition for therapeutic use comprising a compound of claim 1 and a pharmaceutically acceptable carrier or excipient.

13. A method for the treatment of a disease state capable of being modulated by inhibition of phosphodiesterase IV or Tumour Necrosis Factor, which comprises administering to a patient in need thereof an effective amount of a compound of claim 1.

14. The method, according to claim 13, wherein the disease state is a pathological condition associated with a function of phosphodiesterase IV, eosinophil accumulation, or a function of the eosinophil.

15. The method, according to claim 14, wherein the pathological condition is selected from the group consisting of asthma, chronic bronchitis, chronic obstructive airways disease, atopic dermatitis, urticaria, allergic rhinitis, allergic conjunctivitis, vernal conjunctivitis, inflammation of the eye, allergic responses in the eye, eosinophilic granuloma, psoriasis, rheumatoid arthritis, gouty arthritis and other arthritic conditions, ulcerative colitis, Crohn's disease, adult respiratory distress syndrome, diabetes insipidus, keratosis, atopic eczema, atopic dermatitis, cerebral senility, multi-infarct dementia, senile dementia, memory impairment associated with Parkinson's disease, depression, cardiac arrest, stroke, and intermittent claudication.

16. The method, according to claim 14, wherein the pathological condition is selected from the group consisting of chronic bronchitis, allergic rhinitis, and adult respiratory distress syndrome.

17. The method, according to claim 13, wherein the disease state is capable of being modulated by TNF inhibition.

18. The method, according to claim 17, wherein the disease state is an inflammatory disease or autoimmune disease.

19. The method, according to claim 18, wherein the disease state is selected from the group consisting of joint inflammation, arthritis, rheumatoid arthritis, rheumatoid spondylitis and osteoarthritis, sepsis, septic shock, endotoxic shock, gram negative sepsis, toxic shock syndrome, acute respiratory distress syndrome, cerebral malaria, chronic pulmonary inflammatory disease, pulmonary sarcoidosis, asthma, bone resorption diseases, reperfusion injury, graft vs host reaction, allograft rejection, malaria, myalgias, HIV, AIDS, ARC, cachexia, Crohn's disease, ulcerative colitis, pyresis, systemic lupus erythematosus, multiple sclerosis, type 1 diabetes mellitus, psoriasis, Bechet's disease, anaphylactoid purpura nephritis, chronic glomerulonephritis, inflammatory bowel disease, and leukemia.

20. The method, according to claim 13, wherein the disease state is asthma.

21. The method, according to claim 19, wherein the disease state is selected from the group consisting of acute respiratory distress syndrome, pulmonary inflammatory disease, and pulmonary sarcoidosis.

22. The method, according to claim 19, wherein the disease state is joint inflammation.

23. The method, according to claim 13, wherein the disease state is a disease or disorder of the brain.

24. The method, according to claim 17, wherein the disease state is a yeast or fungal infection.

25. A method of gastroprotection which comprises administering to a patient in need thereof an effective amount of a compound of claim 1.

26. A method of providing an analgesic, anti-tussive, or anti-hyperalgesic effect, in the treatment of neurogenic inflammatory disease associated with irritation and pain which comprises administering to a patient in need thereof an effective amount of a compound of claim 1.

27. A method for treating asthma, which comprises co-administering to a patient in need thereof a compound of claim 1 and a second anti-asthma drug.

28. The method, according to claim 27, wherein said second anti-asthma drugs is selected from the group consisting of bronchodilators, steroids, and xanthines.

* * * * *